Aug. 9, 1949. R. G. PITMAN Plant Pat. 863

TANGERINE TREE

Filed April 22, 1948

INVENTOR
R. G. PITMAN

BY A. Yates Dowell

ATTORNEY

Patented Aug. 9, 1949

Plant Pat. 863

UNITED STATES PATENT OFFICE

863

TANGERINE TREE

Robert G. Pitman, Apopka, Fla.

Application April 22, 1948, Serial No. 22,542

1 Claim. (Cl. 47—62)

This invention relates to fruit bearing plants and more particularly to a new and improved variety of tangerine tree and the fruit thereof which has been developed by me and has many desirable characteristics distinguishing it from other known varieties of fruit.

This new and improved variety has been tested by me in southern Florida and its characteristics have been carefully compared with other varieties for the purpose of developing its desirable features.

Among the distinguishing characteristics are the early, uniform, and consistently prolific bearing of the trees, its relatively greater resistance to cold, and the difference in size and growing characteristics from other known varieties. The fruit is consistently larger than that of other tangerine varieties; it is of a lighter color, never turning red; it is of an aromatic, improved flavor and eating quality, with its segments more easily separable, and of constancy in size, shape, and color.

Figure 1:
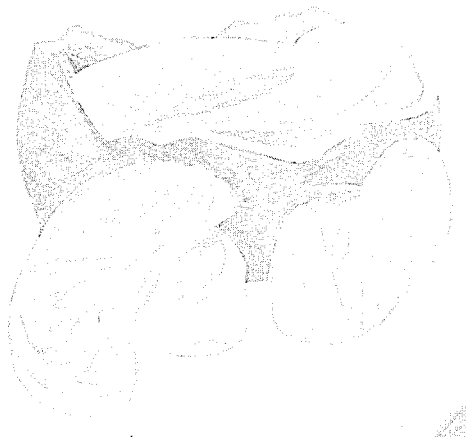
Figure 2:
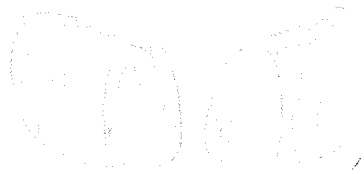
Figure 3:
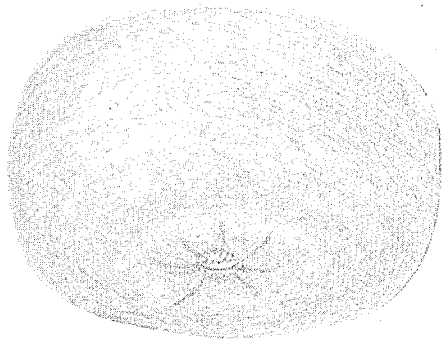
Figure 4:
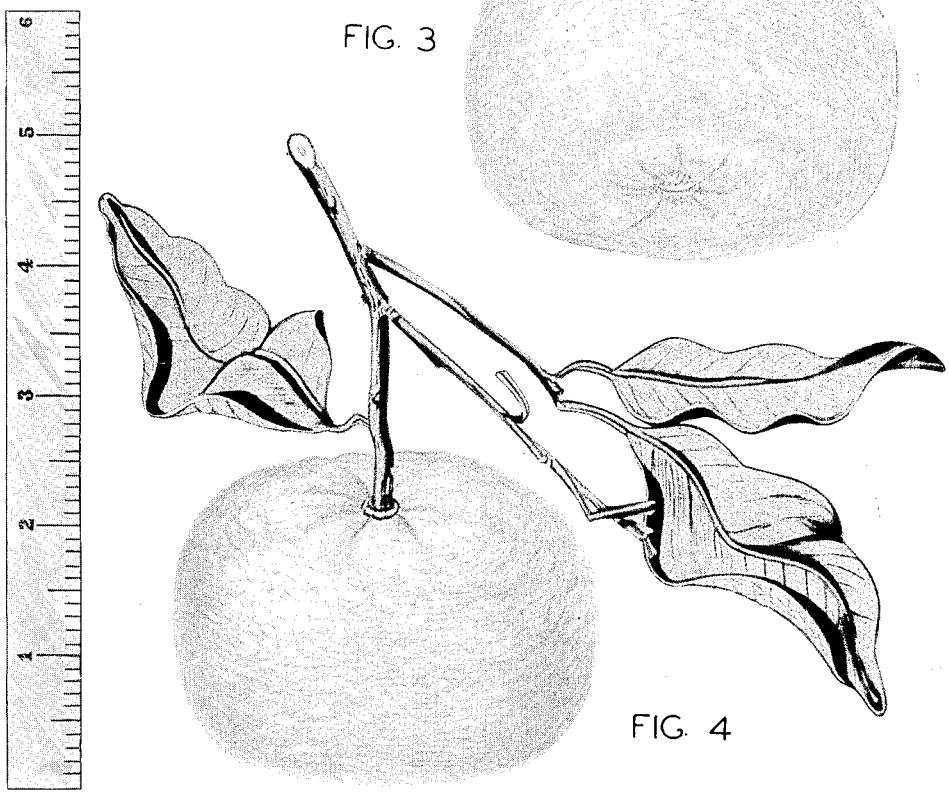

In accordance with these and other characteristics reference is made to the accompanying drawing wherein:

Fig. 1 is a perspective in color and approximately natural size of a fruit with part of the skin and segments removed;

Fig. 2, a perspective of a segment broken to show the vesicles;

Fig. 3, a perspective showing the under side of the fruit; and,

Fig. 4, a perspective of a single fruit and stem with foliage.

The original tree from which budwood was selected, resulting in my new variety, grew from the seed of a Chinese Ponkan. This tree was one of a number which had grown from seed and which had been propagated a limited amount prior to my experience with them. The grove from which the selected tree was taken included trees which were irregular bearers of non-uniform fruit and as a result were unprofitable and never introduced to the trade commercially.

In an attempt to improve the variety by budwood selection I propagated a number of trees and on one a single limb sport grew. This limb appeared to have a slightly different foliage and its fruit ripened earlier, was uniformly larger, and had a distinctive color and flavor. After observing the sport I took budwood from it to produce another generation and compared it with the sport and with a generation produced by budwood from other branches. The new variety remained true to type and has continued to do so through subsequent asexually reproduced generations.

The following is a detailed description of the new variety:

*Tree*

The tree is medium in size and a vigorous grower. Unlike the Ponkan it does not tend to dwarfiness. It is a certain bearer, erect and begins drooping from the weight of the fruit as it matures.

Trunk: Medium.

Branches: Medium to slender; branchlets rounded; spines lacking on old wood, seldom found on new wood.

Leaves: Thin to medium; dark green above, lighter green below; narrower and more pointed than the Dancy.

Flowers: Normal period of bloom March, sometimes early April. The blooms are usually solitary and small.

*Fruit*

Size: Uniformly large.
- *Circumference.*—7 to 10 inches.
- *Axial diameter.*—2 to 3 inches.
- *Transverse diameter.*—2½ to 3½ inches.

Form: Fairly uniform; globose to oblate; symmetrical.
- *Base.*—Flattened.
- *Apex.*—Smooth; rounded.
- *Navel.*—Slightly depressed.

Stem size: Medium; slender. *Position*—straight.

Calyx: Small lobes; simple; triangular; thin.

Rind: Freely separable; close early in season; puffed late in season.
- *Surface.*—Smooth.
- *Flavor.*—Sweet; aromatic; exceedingly pleasant. Thickness—medium.
- *Color.*—Yellow orange, somewhat lighter than the Chinese Ponkan. *Bloom*—abundant.
- *Oil cells.*—Medium.

Segments: 10 to 12.
- *Size.*—Uniform; large; easily separable.
- *Dorsal surface.*—Rounded.
- *Segment walls.*—Thin and tender.

Flesh:
- *Color.*—Deep salmon orange.
- *Texture.*—Fine; tender.
- *Rag in flesh.*—Little.
- *Vesicles.*—Large; plump.
- *Juice.*—Abundant; evenly distributed in sections.

*Flavor.*—Sweet; aromatic; well blended.
*Quality.*—Best.

Seeds: Present—one or two in each segment; small.
*Form.*—Plump, nearly smooth.
*Apex.*—Rounded.
*Color.*—Green.

Pith: Hollow. *Thickness.*—$\frac{1}{16}$ to $\frac{1}{8}$ inch.

Season: Early; from 2 to 3 weeks earlier than the Dancy; substantially the same period as the Ponkan; best shipping season, latter half of October and all of November.

Keeping quality: Good.

Shipping quality: Good.

Resistance to:
*Insects.*—Medium.
*Diseases.*—Good.
*Cold.*—Good.

*General notes*

This tree is slenderer than the Dancy and does not spread or branch out as close to the ground as that variety. It is more upright in habit of growth and requires more pruning for it to spread. Instead of producing fruit at the ends of the branches, it is more inclined to produce fruit along the limbs for some distance up the branch.

The size of the fruit is much larger than that of the Dancy, and its shape is more like that of a Temple orange than a Dancy. The present variety is considered more oblate and flattened than the Temple orange. The color of the fruit is much lighter than the Dancy's deep red.

It is understood that reasonable variations in the characteristics and description of my fruit may occur when produced under different conditions, such as those of climate, soil, stock, fertilizer, location, altitude, and others affecting plant life.

I claim:

A new and distinctive variety of tangerine tree substantially as described, characterized by the early ripening, large size, and distinctive flavor and color of the fruit.

ROBERT G. PITMAN.

No references cited.